(12) United States Patent
Kambara et al.

(10) Patent No.: US 6,841,128 B2
(45) Date of Patent: Jan. 11, 2005

(54) DNA BASE SEQUENCING SYSTEM

(75) Inventors: Hideki Kambara, Hachioji (JP); Guohua Zhou, Koganei (JP); Yuji Miyahara, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 162 days.

(21) Appl. No.: 09/805,240

(22) Filed: Mar. 14, 2001

(65) Prior Publication Data

US 2001/0024790 A1 Sep. 27, 2001

(30) Foreign Application Priority Data

Mar. 17, 2000 (JP) ......................................... 2000-075384

(51) Int. Cl.⁷ ............................................... G01N 30/02
(52) U.S. Cl. .......................... 422/70; 435/6; 435/91.51; 435/91.1; 435/91.2; 422/69; 422/100; 422/101; 422/102; 422/52; 204/452; 536/23.1; 536/25.3; 536/24.3; 536/25.32
(58) Field of Search .............................. 422/52, 69, 70, 422/100, 101, 102; 435/6, 91.51, 91.1, 91.2; 204/452; 536/23.1, 25.3, 25.31, 24.3, 25.32

(56) References Cited

U.S. PATENT DOCUMENTS

| 5,534,424 | A | 7/1996 | Uhlen et al. |
| 6,245,506 | B1 * | 6/2001 | Laugharn et al. ............... 435/6 |
| 6,387,234 | B1 * | 5/2002 | Yeung et al. ............... 204/451 |

FOREIGN PATENT DOCUMENTS

| JP | 62-85863 | 7/1986 |
| JP | 8-500724 | 5/1993 |
| JP | 7-203998 | 1/1994 |
| JP | 09-026426 | 7/1995 |
| JP | 09-972843 | 9/1995 |
| WO | WO 91/06678 | 10/1990 |
| WO | WO 98/28440 | 12/1997 |
| WO | WO 98/52691 | 5/1998 |
| WO | WO 99/33559 | 12/1998 |
| WO | WO 99/66313 | 6/1999 |

OTHER PUBLICATIONS

Ronaghi et al. Science, (1998), vol. 281, pp. 363–365.*
Ronaghi et al., "A Sequencimg Method Based on Real–Time Pyrophosphate," Science, vol. 281 (1998), p. 363–365.

* cited by examiner

Primary Examiner—Samuel Barts
Assistant Examiner—Patrick T. Lewis
(74) Attorney, Agent, or Firm—Reed Smith LLP; Stanley P. Fisher, Esq.; Juan Carlos A. Marquez, Esq.

(57) ABSTRACT

The present invention provides a DNA base sequencing system having a compact, simple and convenient structure.

In one embodiment of the present invention, a reaction chamber module for pyrosequencing in which a multiple number of reaction vessels (reaction chambers) 10 and reagent-introducing narrow tubes 6 are integrated is formed in a device board 5. Reagents held in reagent reservoirs 1, 2, 3 and 4 mounted separately from this reaction chamber module are introduced into the reaction vessels 10 via reagent-introducing narrow tubes (capillaries) 6. The reagent-introducing narrow tubes (capillaries) 6 at the area of 2 cm from the reaction vessels 10 are structured with narrow capillaries having an inner diameter of about 0.1 mm and the conductance of these capillaries for the reagent solution determines the injection speed of the solution.

Using the present invention, many kinds of DNAs can be analyzed simultaneously.

14 Claims, 9 Drawing Sheets

DNA BASE SEQUENCING SYSTEM

BACKGROUND OF THE INVENTION

The present invention relates to assays and analyses of genes or DNAs relating to gene diagnoses, gene therapies, and production of various substances by genes, or the like. In particular, the present invention relates to improvement of pyrosequencing and systems thereof, namely DNA base sequencing methods or sequence monitoring methods and DNA base sequencing systems or sequence monitoring systems.

The progress of the human genome-mapping project is prompting a trend towards conducting diagnoses of diseases and producing useful novel substances at the gene level by reading DNA sequences. However, a big problem remains to be solved: how to quickly analyze a large amount of DNA samples. Although fundamental DNA base sequence data have been almost completely revealed by the genome mapping, it is necessary to compare sequences of various samples with those of standard samples previously sequenced, in order to study sequences of these DNAs and gene functions. Therefore, a large number of various samples have to be quickly sequenced to find differences between the sequences and examine their correlations with biological functions, although the length of the DNAs to be sequenced at a time may be small.

Conventionally, DNAs are sequenced by a DNA base sequencing method using gel electrophoresis, and a DNA sequencer is commercially available and widely used as an apparatus. Recently, a speedy sequencing method is drawing attention, in which a sample DNA is hybridized with a DNA probe using a DNA chip, in which many kinds of DNA probes are immobilized on a solid cell to make a probe array.

On the other hand, a sequencing method different from the above-mentioned methods, called pyrosequencing, has been proposed. In the pyrosequencing method, DNA complementary strand synthesis is monitored to determine sequences, namely, pyrophosphate released as a reaction product upon synthesizing a complementary DNA strand is converted into ATP, which reacts with luciferin using luciferase to generate luminescence. Since pyrosequencing is inexpensive and can be used for sequencing a large number of samples simultaneously, it is a promising method as a high through-put monitor for DNA.

A reported pyrosequencing is briefly explained as follows. The apparatus used is a so-called luminescence photometer. Reagents, including DNA samples; primers to determine the starting point of complementary strand synthesis; DNA synthesizing enzymes; an enzyme apyrase to decompose dNTP (deoxynucleotide triphosphates) which has been added as a substrate and remained unreacted; sulfurylase to convert pyrophosphate into ATP; luciferin; and luciferase involved in the reaction of luciferin with ATP, are placed in a titer plate. At this moment, no complementary strand synthesis occurs because dideoxynucleotides (ddNTPs), a substrate for the reaction, is not present. Four kinds of ddNTPs (i.e., dATP, dCTP, dTTP and dGTP) are added in a designated order by an ink jet system. If dCTP is the designated base to be synthesized, no reaction occurs when dATP, dTTP or dGTP is added. Reaction occurs only when dCTP is added, then the complementary strand is extended by one base length, and pyrophosphate (PPi) is released. This pyrophosphate is converted into ATP by ATP sulfurylase and the ATP reacts with luciferin in the presence of luciferase to emit chemiluminescence. This chemiluminescence is detected using a secondary photon multiplier tube or the like. Remaining dCTP or unreacted dNTP is decomposed by apyrase which converts it into a form which has no effect on the subsequent repetitive dNTP injection and the reaction which follows. The four kinds of dNTP are added repeatedly in a designated order and the base sequence is determined one by one according to the presence or absence of chemiluminescence emitted each time. This series of reactions are shown in FIG. 3 (see Ronaghi, M. et al., Science 281, 363–365 (1998)).

One problem in the current pyrosequencing method, in which ink jet nozzles are used for dNTP injection, is that it requires a considerably large space for the apparatus including a control part for the ink jet nozzles or the like. Another problem is that the target DNA to be provided as a sample in the reaction vessel has to be a single strand, which requires extra labor for the sample preparation. Further, sequencing is not possible in the presence of DNAs, which undergo complementary strand synthesis, other than the target DNA. The reported possible length of DNA to be sequenced ranges between 20 bases and 30 bases. This is because the sequencing is involved in a step reaction, in which the efficiency of the reaction is largely affected by the possible length of the base to be sequenced.

Examples of possible systems in which pyrosequencing is used include a palm-sized DNA sequencer, a DNA sequencer for large scale analyses for gene diagnoses or comparative analyses, and a DNA mutation analysis system. However, for practical use of these systems, several technical problems remain to be solved: (1) how to implement a simple and inexpensive compact apparatus, (2) how to minimize the time required for sample preparation, and how to analyze various samples simultaneously in a simple way, and (3) how to uniformly carry out reactions to increase the reaction efficiency. Accordingly, a compact, inexpensive apparatus and a system which effects simpler sample preparation and sequencing of longer base sequences, if necessary, are needed.

Objects of the present invention are to provide a compact, simple and convenient DNA base sequencing system or a sequence monitoring apparatus, and to provide a DNA base sequencing method or a sequence monitoring method in which sample preparation can be carried out in a simple and easy manner.

SUMMARY OF THE INVENTION

In the present invention, a reaction cell (reaction chamber) and a dNTP-supply route are formed into a module by microprocessing such that the dNTP can be readily supplied by pressurization, whereby the physical size of the required apparatus or system can be minimized. Further, a necessary and sufficient amount of dNTP and reagents can be injected into the reaction area by an efficient supplying method using a simple sample-introducing means instead of an ink jet system or the like, which makes the apparatus small, light and low-cost.

Further, various primers are immobilized on a solid surface, beads or the like, and the target DNA is obtained by hybridizing a double-stranded DNA sample with these primers so that a necessary and sufficient amount of DNA sample can be readily supplied. Since the target DNA can be injected into a reaction vessel without processing it into a single strand, only a simple sample preparation is required for the sequencing reaction.

Longer DNAs can be sequenced and analyzed by carrying out a sufficient and thorough reaction. Therefore, the structure of the reaction vessel is devised such that the reaction chamber is in contact with a vibrating element to thoroughly mix added dNTP with a reaction solution. The reaction efficiency can be increased by stirring the injected dNTP.

In the DNA base sequencing method and system of the present invention, pyrophosphate produced upon a DNA complementary strand synthesis is converted into ATP, the ATP is reacted with luciferin using luciferase to generate chemiluminescence, the emitted chemiluminescence is detected, whereby the kind of incorporated nucleic acid is detected and thus the base sequence is determined. The four kinds of dNTP are supplied into a reaction vessel in a designated order by pressurizing via capillaries or narrow grooves which connect the reaction vessel and reagent reservoirs.

According to the present invention, a palm-sized DNA sequencing apparatus can be made, and many kinds of DNAs can be simultaneously analyzed by providing a multiple number of reaction chambers in a small area Thus the present invention provides the following (1) to (26).

(1) A DNA base sequencing method in which pyrophosphate produced upon synthesizing a strand complementary to a template DNA is converted into ATP, which is reacted with luciferin in the presence of an enzyme such as luciferase, and the complementary strand synthesis is monitored by detecting the resulting chemiluminescence to obtain DNA sequence information, said method comprising supplying four kinds of dNTP into the reaction vessel by pressurizing via independent capillaries or narrow grooves which can be in contact with a reaction solution.

(2) The method described in (1) above, characterized in that each dNTP is supplied in a previously designated order into the reaction vessel by pressurizing each dNTP reservoir in order.

(3) A system to obtain DNA sequence information in which pyrophosphate produced upon synthesizing a strand complementary to a template DNA is converted into ATP which is reacted with luciferin in the presence of an enzyme such as luciferase and the complementary strand synthesis is monitored by detecting the resulting chemiluminescence, said system being characterized by comprising a means for supplying four kinds of dNTP into a reaction vessel via independent capillaries or narrow grooves which can be in contact with a reaction solution, by pressurizing or by a liquid transfer system.

(4) The system described in (3) above, characterized in that the reaction vessel and the dNTP-supply capillaries or narrow grooves are incorporated into one module as a unit.

(5) The system described in (3) above, characterized in that the dNTP-supply capillaries or narrow grooves can be introduced into the reaction solution from the top of the reaction vessel.

(6) The system described in (3) above, characterized in that dNTP is supplied intermittently and repeatedly into the reaction vessel by controlling pressurization of each dNTP reservoir or by controlling an electric field between each dNTP reservoir and the reaction vessel in addition to the pressurization.

(7) A reaction chamber module used in the system described in (3) above, characterized by comprising at least one reaction vessel and at least four lines of capillaries or narrow grooves for reagent introduction corresponding to four kinds of dNTP; said capillaries or narrow grooves having an inner diameter of less than 0.2 mm and/or a cross section area of less than 0.04 $mm^2$, at the inlet of the reaction vessel.

(8) A reaction chamber module used in the system described in (3) above, characterized by comprising at least one reaction vessel and at least four lines of capillaries or narrow grooves for reagent introduction corresponding to four kinds of dNTP; said capillaries or narrow grooves having an inner diameter of less than 0.1 mm and/or a cross section area of less than 0.01 $mm^2$, at the inlet of the reaction vessel.

(9) The reaction chamber module described in (7) above, characterized in that dNTP-containing reaction reagents can be introduced from reagent reservoirs into the reaction vessel via capillaries or narrow grooves at the bottom of the reaction vessel.

(10) The reaction chamber module described in (7) above, characterized in that a supply unit for dNTP-containing reaction reagents and the reaction vessel unit are separable and each reaction agent is alternately and repeatedly supplied from the reaction reagent supply unit installed on the top of the reaction vessel into each reaction solution via capillaries or narrow grooves.

(11) A DNA sequencing method in which pyrophosphate produced upon synthesizing a strand complementary to a template DNA is converted into ATP which is reacted with luciferin in the presence of an enzyme such as luciferase and the complementary strand synthesis is monitored by detecting the resulting chemiluminescence to obtain DNA sequence information, said method being characterized in that a primer which sets a starting point of the complementary strand synthesis is immobilized onto a solid surface, pyrophosphate produced upon synthesizing DNA complementary strand which is hybridized with the primer is converted into ATP which is reacted with luciferin by luciferase or the like, and the DNA base sequence is monitored by detecting the resulting chemiluminescence.

(12) The method described in (11) above, characterized in that different kinds of primers which hybridize with the target DNA are immobilized onto different solid surfaces or different cells having sectioned solid surfaces, the designated reaction is carried out using dNTP after hybridization with the target DNA, and chemiluminescence resulting from the complementary strand synthesizing reaction caused by different primers is distinguished to monitor the sequence.

(13) The method described in (11) above, characterized in that the primers are independently immobilized onto the surface of beads which are spatially separated according to the kind of primer.

(14) The method described in (11) above, characterized in that the solids with the immobilized primers on their surface are held in cells which are spatially separated according to the kind of primer.

(15) A DNA analyzing system which is used in the method described in (11) above.

(16) The DNA analyzing system described in (15) above, characterized in that said system is a detection system capable of distinguishing the position of the chemiluminescence emission.

(17) The DNA analyzing system described in (15) above, characterized in that the chemiluminescence is detected by an area sensor such as a cooled CCD (Charge Coupled Device).

(18) The DNA analyzing system described in (15) above, characterized in that the means for detecting chemiluminescence comprises a chemiluminescence detecting device, such as a photon multiplier tube and an avalanche photodiode, and a system in which the position of the reaction vessel is shiftable relative to a detecting device.

(19) The DNA analyzing system described in (15) above, characterized in that reagents can be supplied without contact with the reaction vessel.

(20) The DNA analyzing system described in (15) above, characterized in that reagents are simultaneously supplied independently to different reaction vessels by an ink jet method or the like.

(21) The DNA analyzing system described in (15) above, characterized in that reagents are supplied to the reaction vessel via capillaries having a diameter of less than 0.2 mm.

(22) A system characterized in that a DNA to be used as a template for complementary strand synthesis is immobilized onto a solid surface, pyrophosphate produced upon synthesizing complementary strand which is hybridized with the DNA is converted into ATP which is reacted with luciferin by luciferase or the like, and the DNA base sequence is monitored by detecting the resulting chemiluminescence, said system being characterized by comprising a means to remove primers and complementary strand synthesis products or to stop the extension reaction by adding dideoxynucleotides(ddNTPs) into the reaction chambers followed by removing dideoxynucleotides(ddNTPs) after the first sequencing process using the primers, to freshly inject primers and enzymes or the like, and to subsequently carry out the second DNA sequencing process, and providing a means to carry out this process repeatedly, if necessary.

(23) The system described in (22) above, characterized by comprising a means in which different kinds of target DNAs (DNA samples) are immobilized onto different solid surfaces or sectioned different cells, the designated reaction is carried out using enzymes and dNTP after hybridization with the primers, and chemiluminescence resulting from the complementary strand synthesizing reaction caused by different primers is distinguished to monitor the sequence.

(24) A DNA base sequencing system, characterized by comprising a reaction vessel, reagent reservoirs each holding any one of four kinds of dNTP, means to supply dNTP into the reaction vessel at least partly consisting of a capillary or a narrow groove, pressurizing means to control the supply of the reagents, means to detect chemiluminescence emitted from the reaction vessel, and means to analyze data to obtain DNA sequence information by processing the detected data.

(25) The method described in (1) above, wherein the same kind of dNTP is added twice to assure that the reaction proceeds thoroughly.

(26) The system described in (3) above, wherein the same kind of dNTP is added twice to assure that the reaction proceeds thoroughly.

This specification includes part or all of the contents as disclosed in the specification and/or drawings of Japanese Patent Application No.2000-75384, which is a priority document of the present application.

EXPLANATION OF NUMBERS IN DRAWINGS 1, 2, 3 and 4: reagent reservoirs for dNTP and the like, 5: device board, 5': microtiter plate, 6: reagent-introducing narrow tube, 6': reagent-introducing groove, 7: secondary photon multiplier tube, 8: amplifier, 9: data processor, 10: reaction chamber, 11: cover mounted with reagent-introducing narrow tubes and capillaries, 12: reagent-introducing capillary;

13: reagent-introducing capillary, 14: upper board of conjugate-type reaction chamber module, 15: lower board of conjugate-type reaction chamber module;

16: middle board of conjugate-type reaction chamber module, 17: lower board of conjugate-type reaction chamber module, 18: washing solution reservoir, 19: introducing-tube conjugating part, 20: capillary-type reaction chamber module, 21: waste solution vessel, 22: partition bead, 23: beads carrying probes and DNAs, 24: cooling CCD camera, 25: data processor;

26: reagent and washing solution inlet, 25: solution outlet, 28: reaction chamber, 29: reaction solution flow route, 30: lower board of conjugate-type reaction chamber module, 31: upper board of conjugate-type reaction chamber module;

32: oscillator.

BEST MODE FOR CARRYING OUT THE INVENTION

The present invention will be described in detail by the following examples referring to the attached drawings.

EXAMPLE 1

Figure 1:
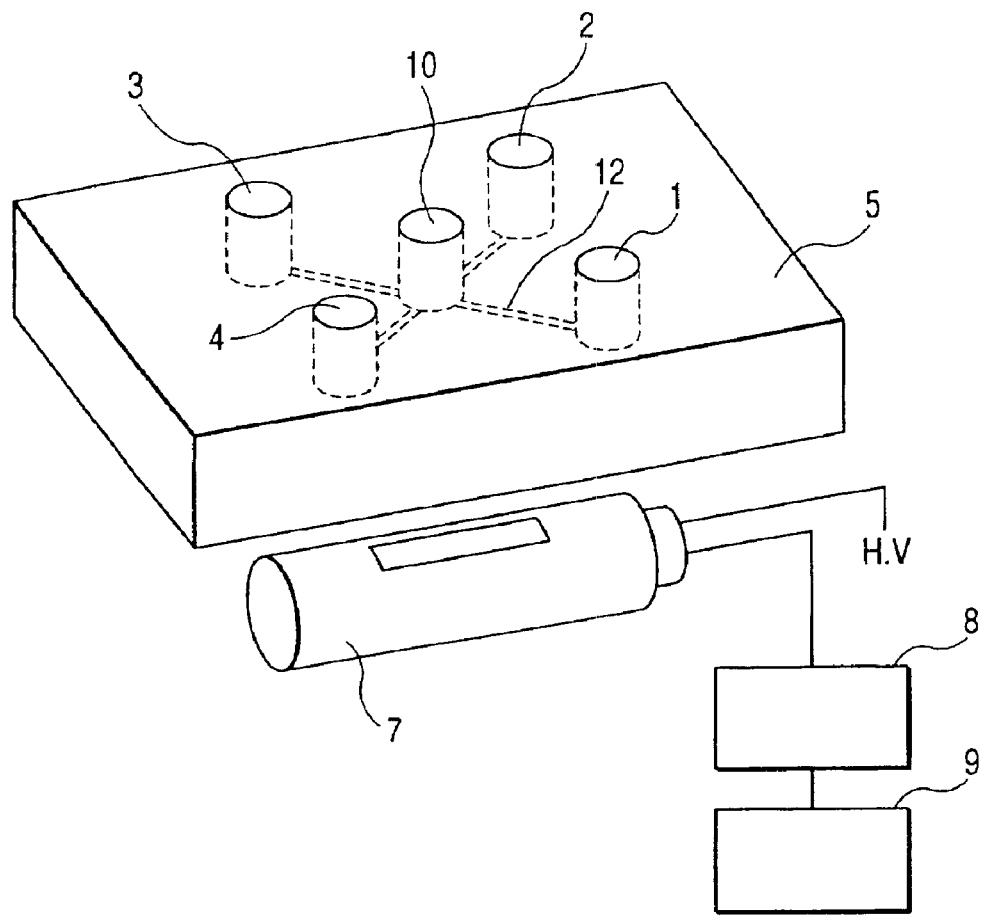
FIG. 1 shows a schematic drawing of a structure example of Example 1 of the present invention showing a DNA base sequencing system having one reaction vessel and dNTP reagent reservoirs.

FIG. 1 shows a structure example of Example 1 according to the present invention, which is a pyrosequencing device (DNA base sequencing system) having one reaction vessel and dNTP reagent reservoirs. A reaction chamber module comprises a reaction chamber (reaction vessel) 10 and reagent reservoirs 1, 2, 3 and 4 each holding one of four kinds of dNTP, all formed on a device board 5. The reaction chamber 10 and each reservoir are connected by capillaries 12 for reagent introduction, through which dNTP from each reagent reservoir is supplied into the reaction vessel for use in the reaction. dNTP is allowed to flow into reaction chamber 10 by pressurizing the liquid surface of each reagent reservoir. It is necessary to suppress a backward flow of the reaction solution and to prevent flow of the reagents into other sites due to a slight difference in the level of liquid surface. Therefore, capillaries having an inner diameter of less than 0.1 mm or a cross section of less than 0.01 $mm^2$ are used. In this Example, the reaction chamber 10 and the reagent reservoirs 1–4 are connected by the glass capillaries 12. However, narrow grooves formed by microprocessing can be used as tubes for reagent introduction.

Figure 2:
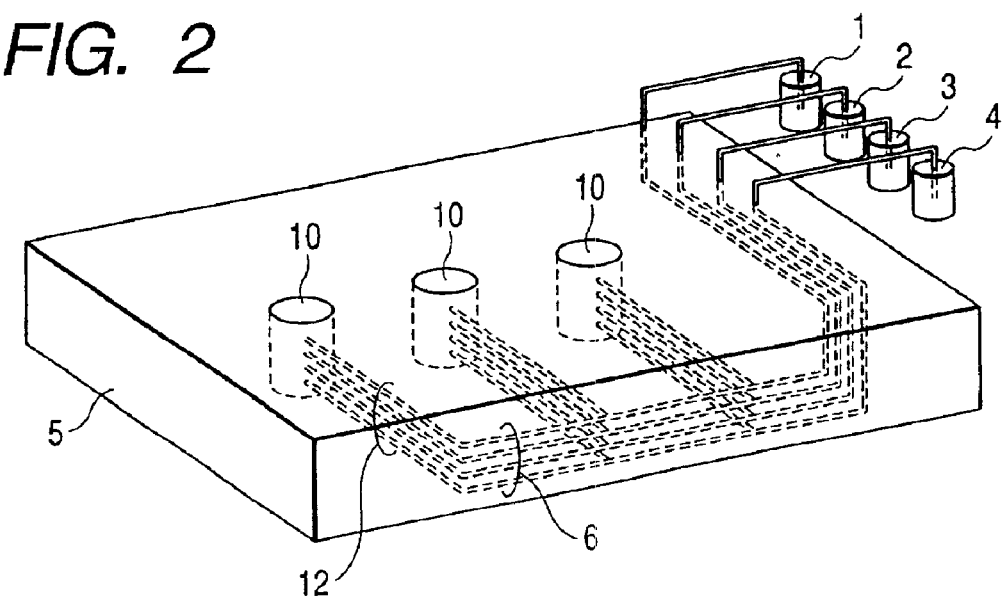
FIG. 2 shows a schematic drawing of another structure example of Example 1 of the present invention showing a reaction chamber module in which a multiple number of reaction vessels are installed and reagent reservoirs mounted on the exterior are connected by tubing with the multiple number of reaction vessels.

FIG. 2 shows another structure example of Example 1 according to the present invention, which is a reaction chamber module of a pyrosequencing device (DNA base sequencing system) having a multiple number of reaction vessels which are connected with reagent reservoirs mounted on the exterior, by tubing. FIG. 2 shows an example of a reaction chamber module in which a multiple number of reaction vessels (reaction chambers) 10 and reagent-introducing narrow tubes 6 are formed as a unit on a device board 5. Reagents are held in reagent reservoirs 1, 2, 3 and 4, which are separated from this reaction chamber module, and introduced into the reaction chamber 10 via reagent-introducing narrow tubes 6. The reagent-introducing narrow tubes 6 at the area of 2 cm from the reaction chambers 10 are structured with narrow capillaries 12 having an inner diameter of about 0.1 mm and the conductance of these capillaries for the reagent solution determines the injection speed of the solution.

The reaction chamber modules shown in FIG. 1 and FIG. 2 are placed inside of a blacked-out box or the like to shield the light from outside, in the same manner with the reaction chamber modules shown in FIG. 5 through FIG. 10. The upper part or the lower part of the reaction area in the reaction chamber modules shown in FIG. 1 and FIG. 2 is constructed with a transparent member to form a window through which the chemiluminescence is led to a detector 7. The chemiluminescence is detected directly through the window, or condensed using a condenser, or guided with an optical fiber or the like and then detected by a photon multiplier tube (PMT). The detection is also carried out by an area sensor such as a cooled CCD. Also, a plane or convex reflector can be effectively installed on the light receiving side and its opposite side in order to enhance detectable light.

Reagents such as a template DNA, DNA polymerase, ATP sulfurylase, apyrase, luciferin, and luciferase are injected into the reaction chamber 10 of the reaction chamber module. On the other hand, a buffer solution and dATP, dCTP, dGTP and dTTP are each injected into the four reaction reagent reservoirs 1, 2, 3 and 4. The capillaries which connect the reaction chamber 10 and the reagent reservoirs 1–4 are filled with a reaction solution, which does not cause any problem in operation. Further, the capillaries can be made of a hydrophobic material to prevent liquid from flowing-in at the start. In that case, air but not liquid exists inside the capillaries and liquid does not flow before the reaction starts. In any case, there is virtually no problem because dNTP is injected into the reaction vessel by pressurization for reaction. Reagents are injected into a specified reaction chamber and the four kinds of dNTP are introduced into the reaction chamber in a designated order by pressurizing the four dNTP reagent reservoirs one by one to carry out the complementary strand synthesis. If dATP is added when a base to be incorporated into the complementary strand is A, the complementary strand is elongated by one base and pyrophosphate is released as a reaction product. The pyrophosphate is converted into ATP by ATP sulfurylase and this ATP then reacts with luciferin to emit chemiluminescence with the aid of luciferase.

Figure 3:
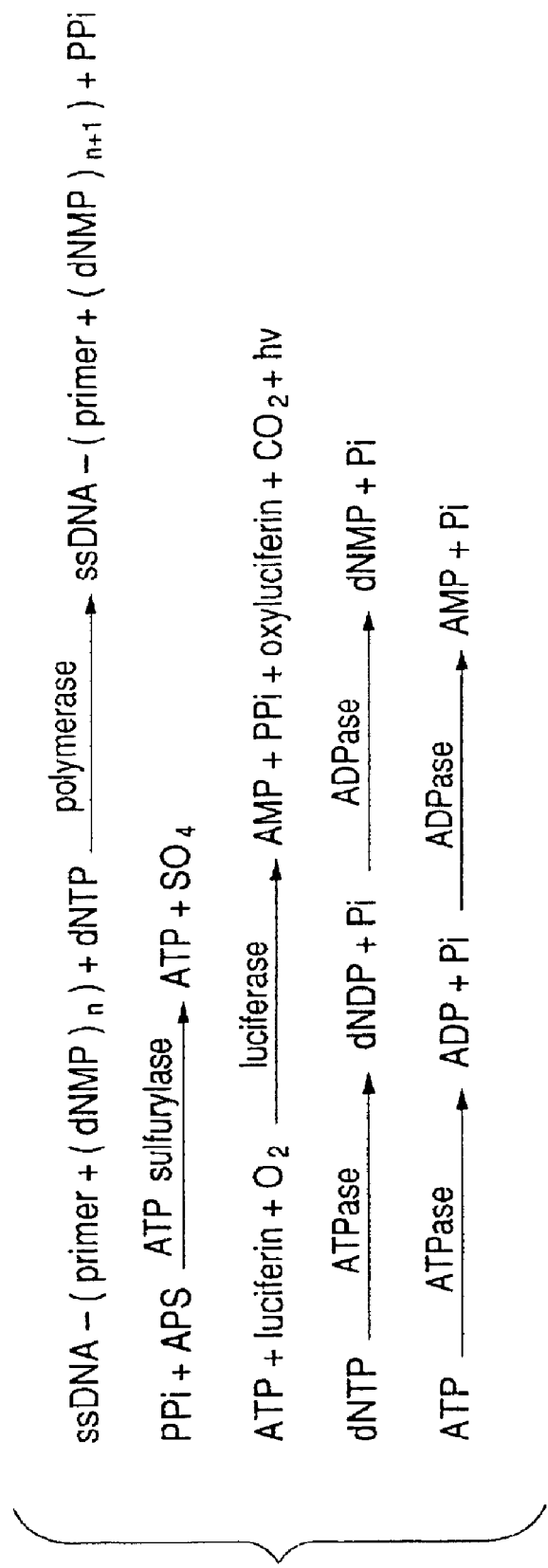
FIG. 3 shows equations for a series of reactions which take place in pyrosequencing of Example 1 of the present invention.

FIG. 3 shows a series of the reactions which take place in the pyrosequencing in Example 1. The emission occurs immediately after reagent injection, and the signal is intensified and then instantly weakened since excess dATP is decomposed by apyrase. Namely, the luminescence signal is observed as a peak as time elapses. On the other hand, if dNTP other than the one to be incorporated into the complementary strand is added, no reaction takes place and so no emission occurs. In this manner, the DNA base sequence is determined by monitoring the presence or absence of chemiluminescence during the process in which the complementary strand is synthesized step by step while exchanging the kind of dNTP added. If the reactions are not thoroughly carried out, reactions for each DNA chain proceed unevenly, which interferes with the base sequencing.

Figure 7:
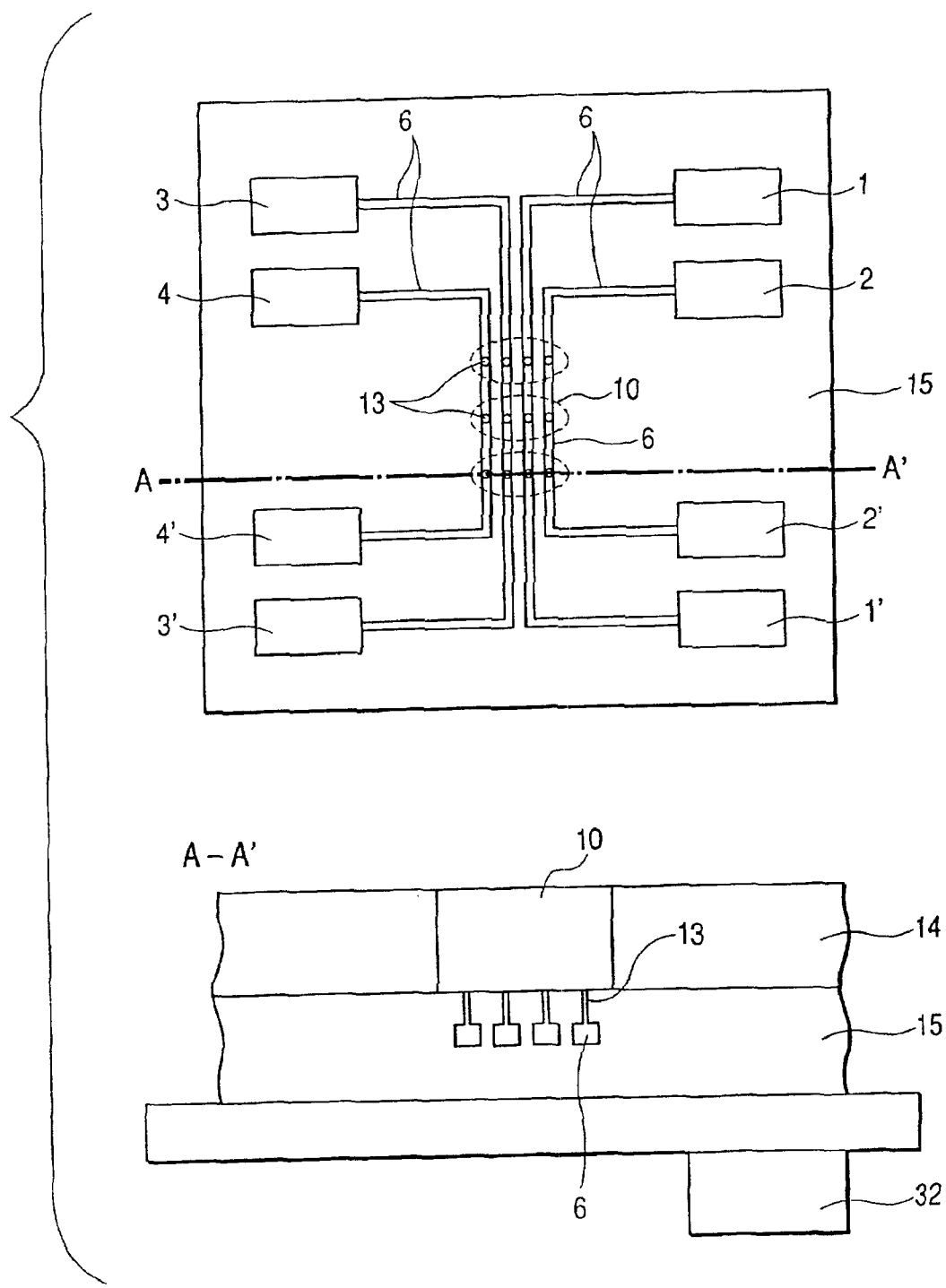
FIG. 7 shows a schematic drawing of a structure example of Example 3 of the present invention showing a reaction chamber module in which a multiple number of reaction vessels and reagent reservoirs are installed and reagents are supplied into the reaction vessels using narrow tubes.

Therefore, a device which vibrates the reaction chamber module can be installed to make the reactions even. For example, as shown in FIG. 7, an oscillator 32 with a frequency of 20 kHz can be used. However, the device is not particularly restricted and need not be an oscillating device, and any device capable of stirring the reaction solution can be used. Furthermore, the sequencing can be carried out by adding the same kind of dNTP twice at a time to ensure a thorough progress of the reaction.

Chemiluminescence emitted at the reaction vessel of the reaction chamber module shown in FIG. 1 and FIG. 2 is received by a photon multiplier tube 7 or the like and then introduced into a computer (data processor) 9 via a current/voltage amplifier 8, AD converter, or the like to process data and output the result of base sequencing.

Figure 4:
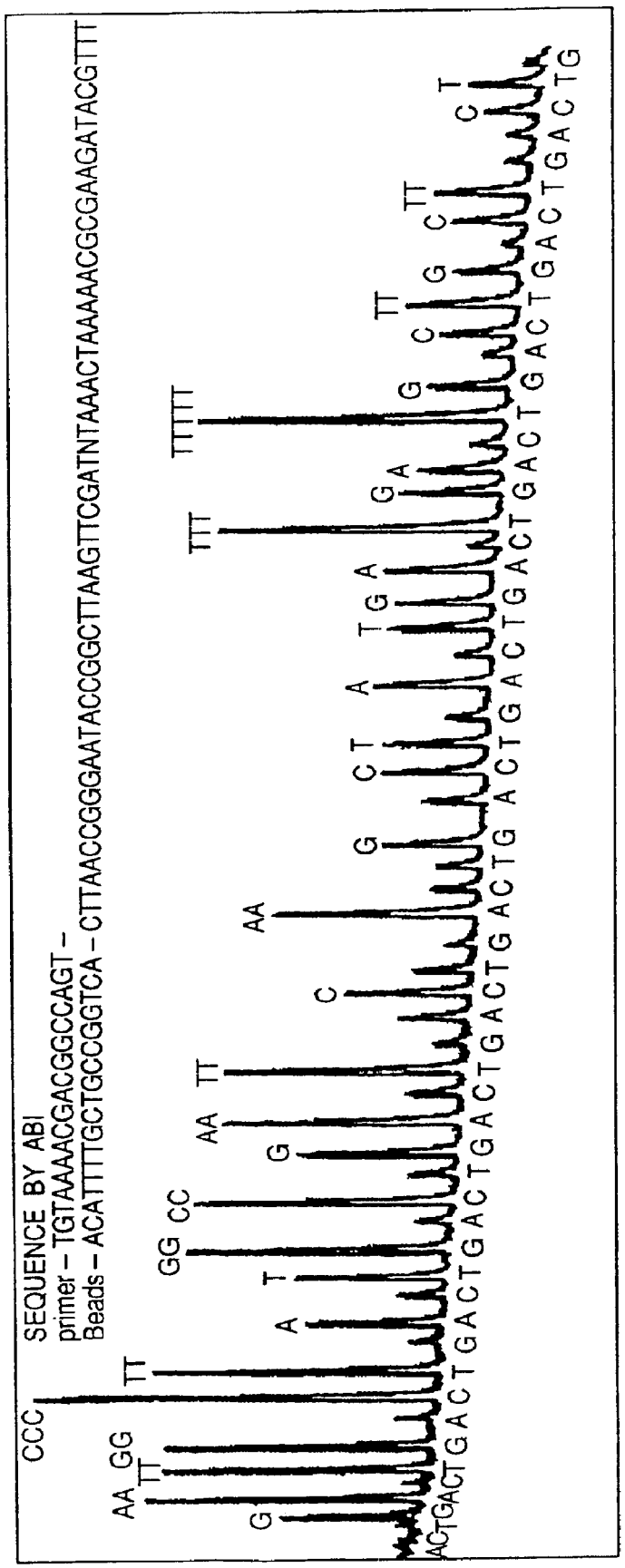
FIG. 4 shows a chart showing an example of emission signals obtained in an experiment using the structure of Example 1 of the present invention. Vertical axis:emission intensity; horizontal axis:time.

FIG. 4 shows an example of chemiluminescence signals obtained in an experiment using the structure of Example 1. The vertical axis is the intensity of chemiluminescence and the horizontal axis is the time elapsed.

dNTP reagents are repeatedly added to the reaction vessel in the order of dATP, dCTP, dTTP and dGTP. Although emission occurs corresponding to every addition, strong chemiluminescence is emitted when the complementary strand synthesis occurs. When no complementary strand synthesis occurs, essentially no pyrophosphate is produced. However, because of impurities or the like contained in the reagents, weak chemiluminescence may be observed. The sequencing can be done by sequentially recording the kinds of injected dNTP when a strong chemiluminescence signal is generated. The amount of produced pyrophosphate increases when the same kind of bases appears side by side and the same kind of bases are successively incorporated. The strength of emission is increased about two-fold when two bases are incorporated, and about three-fold when three bases are incorporated. The complementary strand synthesis reaction so carried out is not necessarily complete. As the reaction proceeds, the amount of unreacted DNA strands increases, and as a result, chemiluminescence can be observed even when dNTP is added for which essentially no emission should occur. In this way, the limit of the length of the DNA to be able to be sequenced is virtually determined. FIG. 4 shows an example in which a strand of more then 50 bases can be sequenced.

EXAMPLE 2

Figure 5:
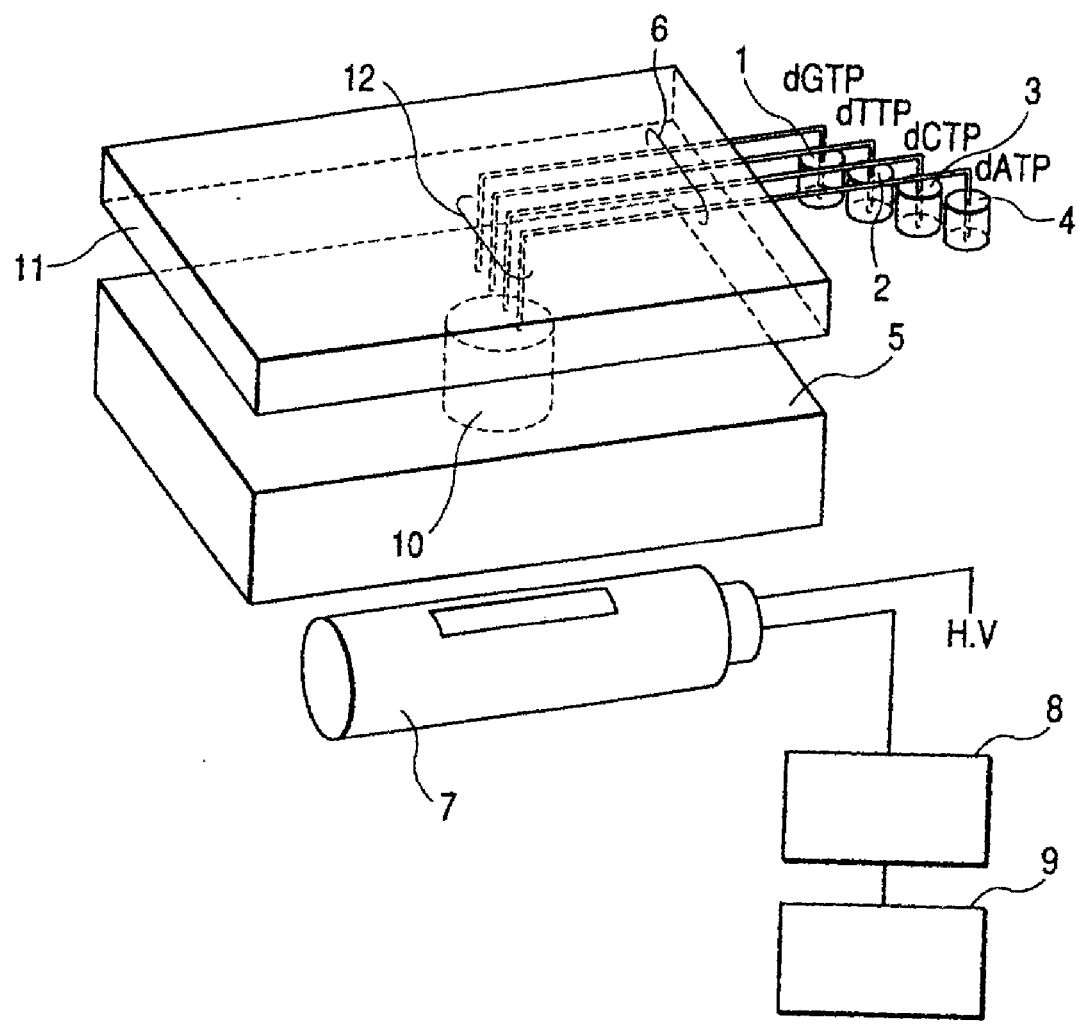
FIG. 5 shows a schematic drawing of a structure example of Example 2 of the present invention showing one type of pyrosequencing device (DNA base sequencing system) in which dNTP is injected into a reaction vessel via a capillary from the top.

FIG. 5 is a structure example of Example 2, showing one type of pyrosequencing device (DNA base sequencing system) in which dNTP is injected into a reaction vessel via capillaries from the upper part. In Example 2, reagents are injected from the upper part of the reaction chamber 10. The reaction chamber module of Example 2 is composed of the reaction vessel (reaction chamber) 10 formed on a device board 5 and a cover (reagent supply unit) 11 which is separable from the device board 5. The upper part of the reaction chamber 10 is covered with the cover 11 which is equipped with reagent-introducing narrow tubes 6 and reagent-introducing capillaries (capillaries) 12. The capillaries 12 in Example 2 have an increased inner diameter of 0.2 mm since the part of the capillaries in contact with the reaction chamber 10 is longer than that in Example 1. The conductance of the capillary having an inner diameter of 0.2 mm for the reagent solution determines the injection speed of the solution. The reaction chamber 10 and the cover 11 can be made airtight and the reagents are supplied into the reaction chamber 10 from reagent reservoirs 1, 2, 3 and 4 by pressurization in the same manner as described in Example 1. For pressurization, a pump was used, but a drop between each reagent reservoir 14 and reaction chamber 10 can also be used. When the drop is used, the height of the reservoir 1–4 for four kinds of reagents has to be changed alternately. Reagent injection can also be controlled with an electric field by applying an osmotic flow generated by electrolysis while maintaining the drop at a fixed level. Furthermore, a liquid-supplying pump used for a microsystem can also be used. A voltage of 1 kV to 2 kV is applied between the reaction chamber 10 and each reagent reservoir 1–4 to generate the osmotic flow from the reaction chamber 10 to the reagent reservoirs 14. The direction of this osmotic flow is opposite to the liquid flow generated by the drop and virtually balanced. The reagent is supplied into the reaction chamber when the direction of the electric field is reversed and the flow from the drop and the osmotic flow are in accord. Accordingly, this kind of system in which reagents are supplied via capillaries installed on the cover section of the upper part of the reaction vessel is effective when many kinds of DNA samples are to be sequenced.

Figure 6:
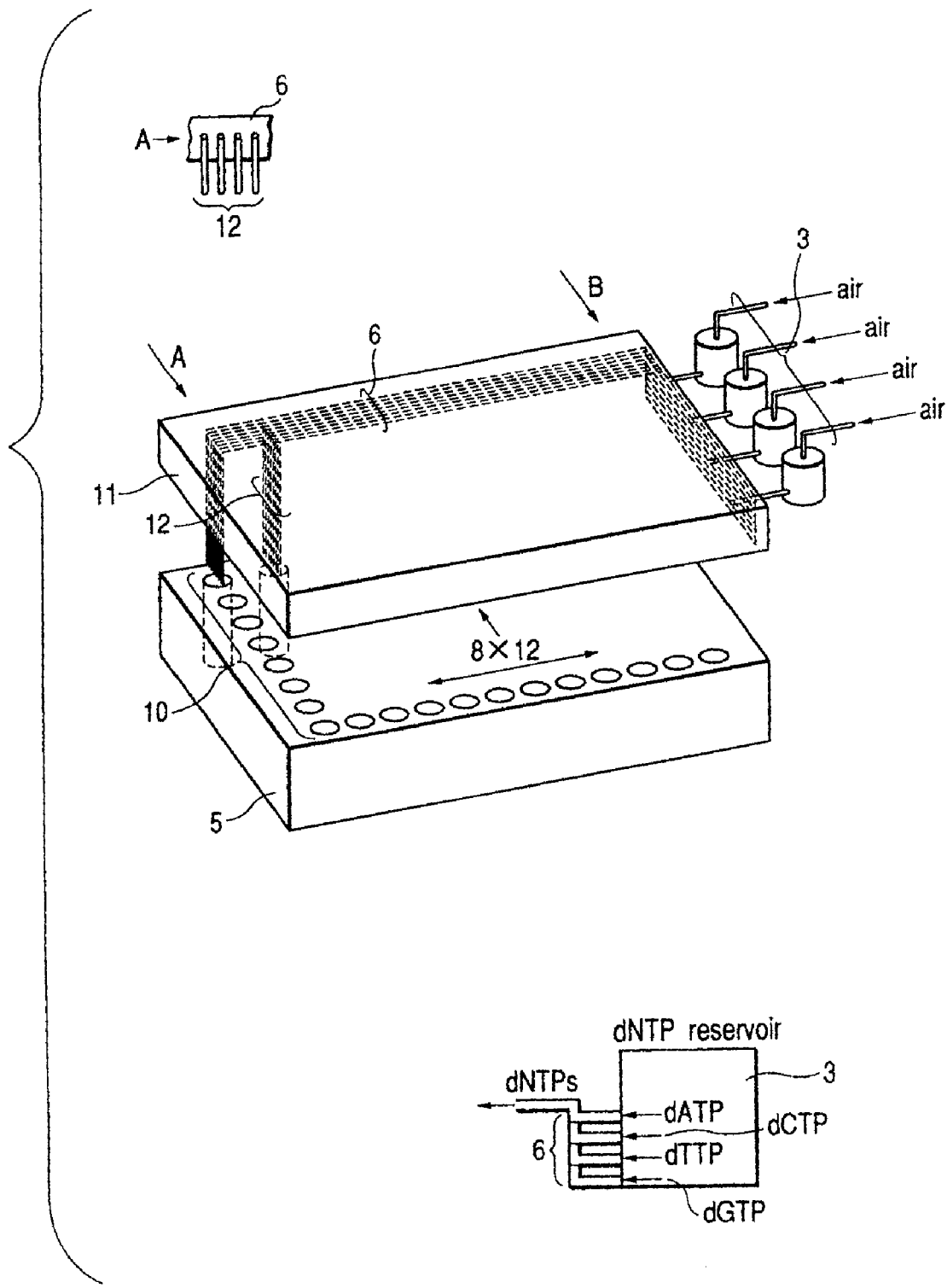
FIG. 6 shows a schematic drawing of another structure example of Example 2 of the present invention showing a reaction chamber module in which a multiple number of reaction vessels are installed and four kinds of dNTPs in reagent reservoirs mounted on the exterior are injected in a designated order into the multiple number of reaction vessels via capillaries from the top.

FIG. 6 is another structure example of Example 2 of the present invention, showing another type of device (reaction chamber module) in which a multiple number of reaction vessels are installed and dNTP in reagent reservoirs mounted on the exterior is injected in a designated order into the reaction vessels through tubing via capillaries from the upper part. In the structure example given in FIG. 6, a multiplicity of reaction vessels (reaction cells) on a microtiter plate 5 is used as reaction chambers 10. The cover 11 on the top is tightly placed on the top of the microtiter plate so that the reaction vessels (reaction chambers, reaction cells) 10 are tightly sealed. On the cover 11, four reagent-introducing capillaries 12 are mounted for each reaction cell to supply each dNTP into each reaction cell. The reagent-introducing capillaries 12 are independently connected to reagent reservoirs 1, 2, 3 and 4 via thick reagent-introducing narrow tubes 6. When the reagent reservoirs are pressurized, reagents are supplied into the reaction chambers 10 via the capillaries 12. The reactions then take place as described above.

EXAMPLE 3

FIG. 7 is a structure example of Example 3 of the present invention, showing a conjugate-type reaction chamber module of a DNA sequencing system, in which a multiple number of reaction vessels and a multiple number of reagent reservoirs are installed and reagents are supplied into reaction vessels using narrow tubes formed by microprocessing or the like.

In the example of the conjugate-type reaction chamber module shown in FIG. 7, reaction reagents are supplied from the lower part of the reaction chambers 10. In the conjugate-type reaction chamber module, an upper board 14 having a multiple number of holes to be made into reaction chambers 10 are formed and the lower board 15 comprising a multiple number of reagent reservoirs 1, 2, 3, 4, 1', 2', 3' and 4' and reagent-introducing capillaries (narrow grooves) 13 are formed and conjugated such that the multiple number of reaction chambers 10 are formed by the conjugation between the upper board 14 and the lower board 15. A reagent reservoir 1 and a reagent reservoir 1', a reagent reservoir 2 and a reagent reservoir 2', a reagent reservoir 3 and a reagent reservoir 3' and a reagent reservoir 4 and a reagent reservoir 4' are connected via reagent-introducing narrow tubes 6, respectively, and the reagent-introducing narrow tubes 6 and the reaction chambers 10 are connected via narrow grooves 13. dNTP is supplied from the narrow grooves 13 formed in the bottom of the reaction chambers 10.

The reaction chamber module in Example 3 can be easily washed and repeatedly used. The four kinds of dNTP can be held independently in reagent reservoirs 1, 2, 3 and 4 and supplied into the reaction vessels 10 in a designated order by pressurization. In the structure given in FIG. 7, two reagent reservoirs are installed for each dNTP. This is for the purpose of pushing out air bubbles or the like into the opposite side by pressurizing the reagent reservoirs from one side in case air bubbles or the like enter the reagent-introducing narrow tubes 6 which supply a reaction solution. The reagent-introducing narrow tubes 6 and the reaction chambers 10 are connected by capillaries 13. The inner diameter of the capillaries is smaller than that of the reagent introducing narrow tubes 6 and the pressure loss upon pressurizing the reagent reservoirs occurs virtually at the site of the capillaries 13. When the DNA complementary strand synthesizing reaction takes place, chemiluminescence is emitted according to the above-mentioned reactions and detected by a light detector in the same manner as described in Examples 1 and 2. On the upper board 14, holes connected to the reagent reservoirs are formed for pressurization. Furthermore, an oscillator 32 is installed to vibrate the reaction chamber module in order to carry out the reaction evenly.

In this example, the capillaries are made as narrow grooves 13; however, capillaries can be installed in the vertical direction at the bottom of the reaction chambers to supply reagents. This embodiment is effective for a module in which a multiplicity of reaction chambers are installed.

Figure 8:
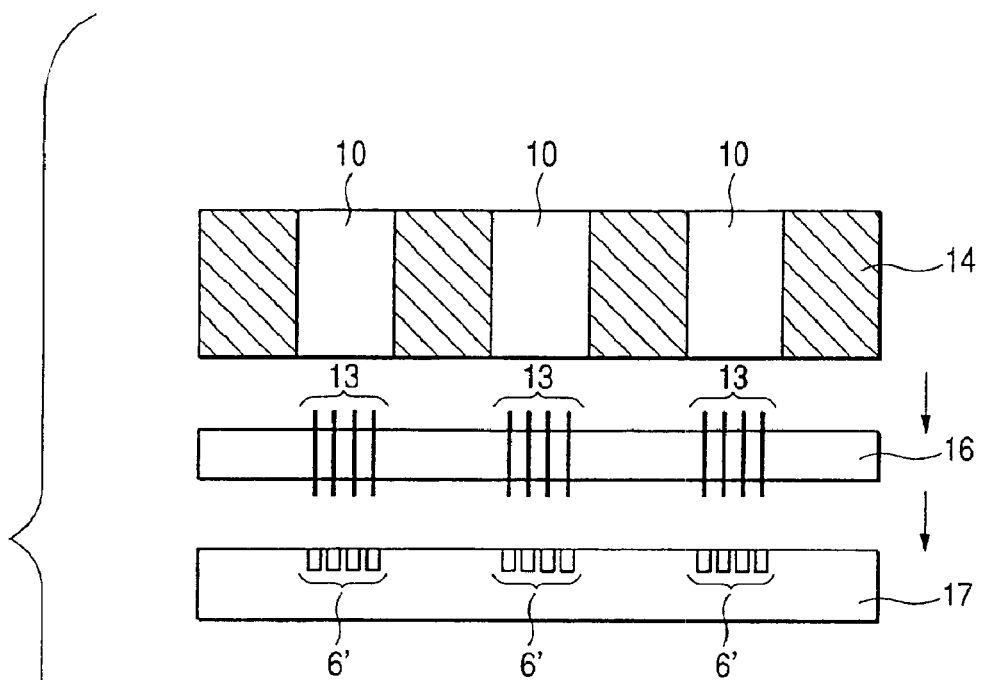
FIG. 8 shows a schematic drawing of another structure example of Example 3 of the present invention showing a reaction chamber module in which reagent reservoirs are mounted on the exterior and reagents are supplied into a multiple number of reaction vessels using grooves.
Figure 8:
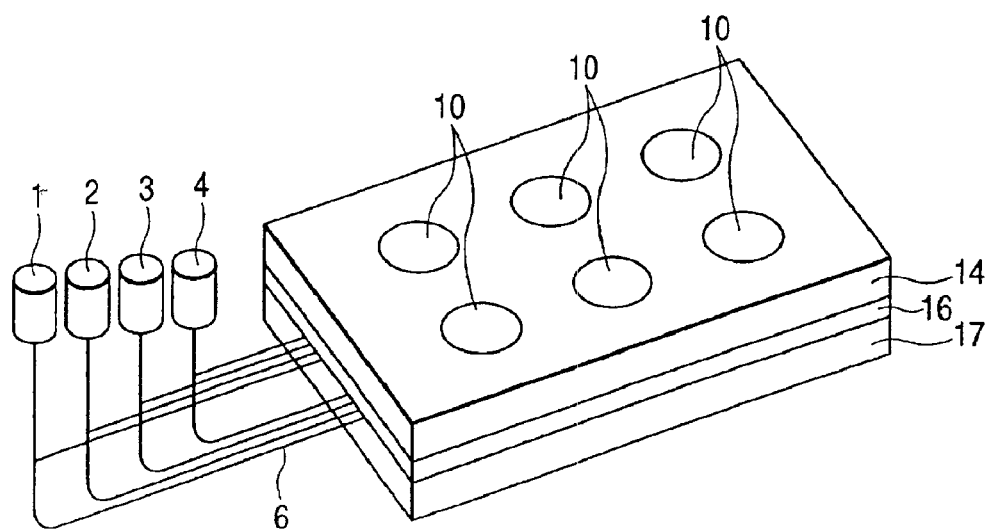

FIG. 8 is another structure example of Example 3 of the present invention, showing a conjugate-type reaction chamber module of a DNA sequencing system, in which reagent reservoirs are installed on the exterior and reagents are supplied into a multiple number of reaction vessels via grooves formed by microprocessing or the like. In the example of the conjugate-type reaction chamber module shown in FIG. 8, reaction reagents are supplied from the lower part of the reaction chambers 10 in the same manner as the conjugate-type reaction chamber module shown in FIG. 7. In this conjugate-type reaction chamber module, an upper board 14 comprising a multiple number of holes comprising reaction chambers 10, a middle board 16 in which four reagent-introducing capillaries 13 to supply dNTP corresponding to each reaction chamber 10 are buried, and a lower board 17 having four reagent-introducing grooves 6' corresponding to the four reagent-introducing capillaries 13 are conjugated, and thus a multiple number of independently separated reaction chambers 10 are formed by the conjugation between the upper board 14 and the middle board 16. The four reagent-introducing grooves 6' corresponding to each reaction chamber and reagent reservoirs 1, 2, 3 and 4 are connected by reagent-introducing narrow tubes 6 and reagents are supplied into each reaction chamber via the capillaries 13. The reaction chamber module structure shown in FIG. 8 can be easily washed and repeatedly used. The four kinds of dNTP independently held in reagent reservoirs 1, 2, 3 and 4 are supplied in a designated order into each reaction chamber 10 via narrow tubes 6, grooves 6' and then capillary 13 by pressurizing. The grooves 6' and the reaction chambers 10 are connected by capillaries 13. The inner diameter of the capillaries 13 is smaller than that of the narrow tubes 6 so that pressure loss upon pressurization virtually occurs at the site of capillaries 13. When the DNA complementary strand synthesizing reaction takes place, chemiluminescence is emitted according to the above-mentioned reactions, and detected by a light detector in the same manner as described in Examples 1 and 2. Although six reaction chambers are shown in the example of the reaction chamber module in FIG. 8, the reaction vessel can also be made to have the same pitches as those of the wells of a 96-well titer plate.

In the above-mentioned Example 1 to Example 3, sample DNAs which were previously prepared as single strands were placed independently in different reaction cells (reaction chambers) with primers, polymerase and other reagents, and the designated pyrosequencing reactions were carried out to determine the sequences.

EXAMPLE 4

Samples to be sequenced include multiple kinds of DNA, one DNA having a multiple number of sites to be sequenced, or ones to be sequenced repeatedly step by step. Example 4 relates to an effective DNA sample supply in a case where a multiple number of sites have to be sequenced (see FIG. 6 through FIG. 10). In this example, a multiplicity of samples are effectively sequenced. Different primers are used depending on targets to be sequenced. The primers are immobilized on the surface of solids such as pellets and beads, or on sectioned solid surfaces or independently different bead surfaces, and held in reaction cells (reaction vessels, reaction chambers) in a spatially distinguishable arrangement. Next, a DNA sample is introduced into a reaction vessel for hybridization with the immobilized primers which trap DNAs having a designated sequence. After discharging and removing the solution containing remaining DNAs, the reaction solution is injected and pyrosequencing is carried out according to the procedure described above. The site of emission is distinguished using a site-detectable CCD array sensor, a detector capable of shifting detection sites applying cofocal point microscope technology, or the like. Thus, DNAs attributable to complementary strand synthesis products responsible for the emission can be distinguished.

EXAMPLE 5

Example 5 is an embodiment of a system in which dNTP decomposing enzymes such as apyrase are not used in the reaction. Beads on which DNAs are immobilized are placed in a reaction cell which is composed of a capillary or the like. The reaction cell can be square-shaped such as a spectral cell. When a multiple number of DNAs are to be sequenced simultaneously, in order to distinguish DNAs to be sequenced, beads carrying immobilized DNAs are sorted and held in different sections or held in different cells.

Figure 9:
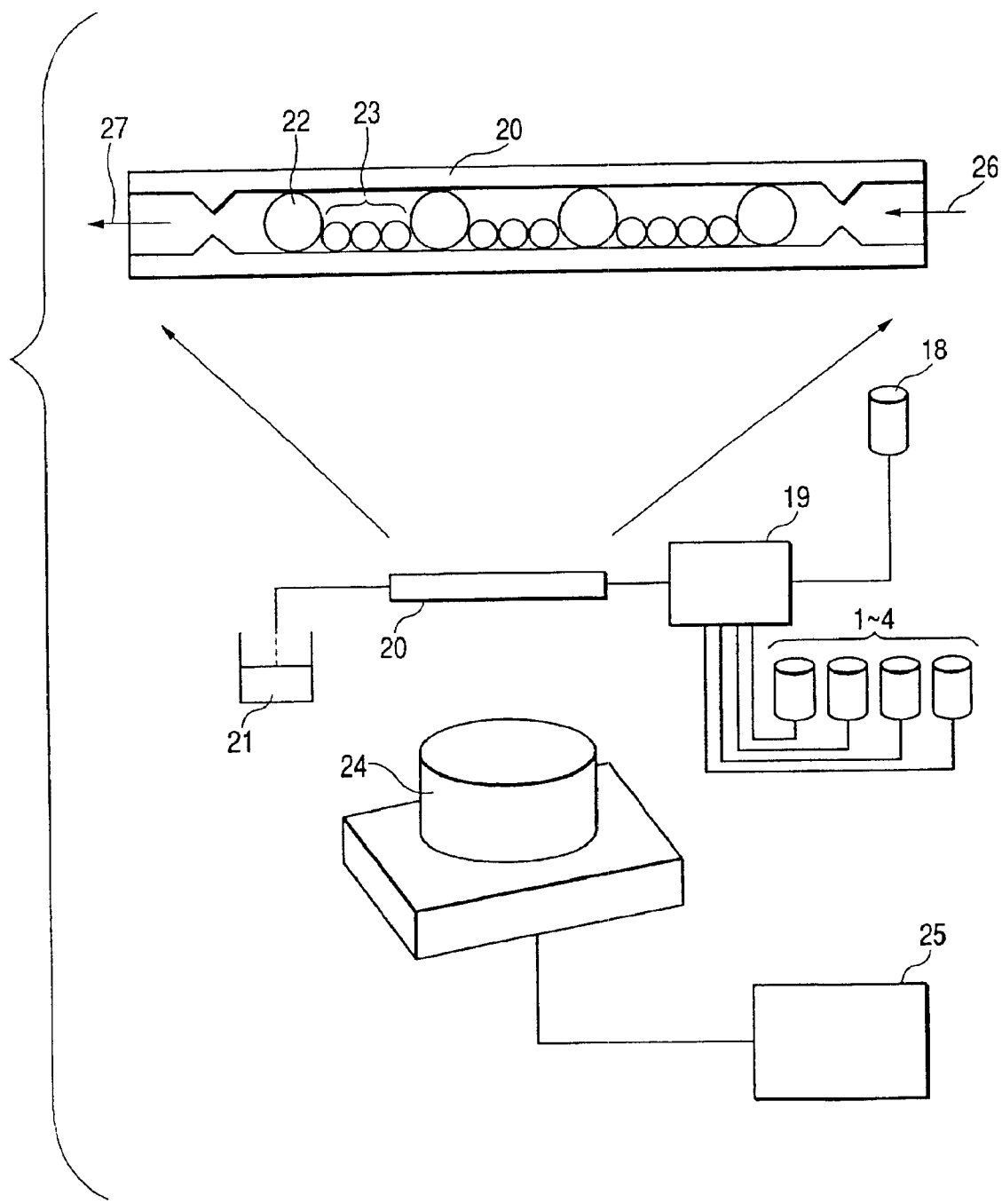
FIG. 9 shows a schematic drawing of a structure example of Example 5 of the present invention showing a DNA base sequencing system in which DNAs and primers are held on beads in a capillary and a complementary strand synthesis is carried out step by step by supplying reagents into the capillary.

FIG. 9 is a structure example of Example 5 of the present invention, showing a DNA sequencing system in which DNAs and primers are held on beads placed in a capillary and complementary strand synthesis can be carried out step by step by pouring reagents into the capillary. Inside the capillary-type reaction vessel 20, beads 23 carrying immobilized probes and DNAs are aligned. Partition beads 22 are placed between the beads 23 carrying different kinds of DNA so that reaction products are not mixed. The diameter of the partition beads 22 is slightly smaller than the inner diameter of the capillary-type reaction vessel 20 and the diameter of beads 23 is smaller than that of partition beads 22 so that the beads 23 will not be moved out beyond the partition beads 22 when a reaction solution or a washing solution is poured into the capillary 20. Stoppers are formed at a reagent and washing solution inlet 26 and a solution outlet 27 to prevent the partition beads 22 in the capillary-type reaction vessel 20 from flowing out. After placing the partition beads 22 and the beads 23 carrying immobilized probes and DNAs in this way, a solution containing reaction reagents is injected into the reaction vessel 20 from one of the reagent reservoirs 1, 2, 3 and 4 via the reagent and washing solution inlet 26. The four kinds of dNTP are repeatedly injected in a designated order. After completion of the injection and then the reaction with one dNTP, a washing solution from a washing fluid reservoir 18 is poured into the reaction vessel 20 via the reagent and washing solution inlet 26 by shifting an introducing-tube conjunction part 19 to dispose of the reaction solution via the solution outlet 27 into a waste solution vessel 21. Thereafter the next dNTP is introduced. A capillary having an inner diameter of about 0.1 mm to 0.3 mm is used as the capillary-type reaction vessel 20. The liquid necessary for the reaction is no more than several micro liters and even the volume of reagents consumed during 100 repetitive reactions is extremely small and almost negligible as compared to the volume used in conventional methods.

If the DNA complementary strand synthesis reaction takes place upon the injection of one of the dNTP, the above-mentioned reactions take place, the emission occurring near the very beads 23, where the DNA complementary strand synthesis reaction takes place, is then detected by a cooled CCD camera 24 in the example shown in FIG. 9, and the detected chemiluminescence signal is processed by a data processor 25 for base sequence determination in the same manner as described in Examples 1 and 2.

The above explanation is for a structure in which a multiple number of DNAs are simultaneously sequenced using a capillary-type reaction vessel 20. However, a multiple number of DNAs can be simultaneously sequenced using a board-type reaction vessel having a multiple number of sections (cells) in which beads 23 carrying probes and DNAs are held. The four kinds of dNTP are repeatedly injected in a designated order into a multiple number of sections (cells) of the board-type reaction vessel. After completion of the injection of and then the reaction with one dNTP, a washing solution is poured into each section (cell) to remove the reaction solution; thereafter the next dNTP is introduced. If the DNA complementary strand synthesis reaction takes place upon the injection of one of the dNTP, the above-mentioned reactions take place, and the emission occurred at the section (cell) where the DNA complementary strand synthesis reaction takes place is then detected.

Figure 10:
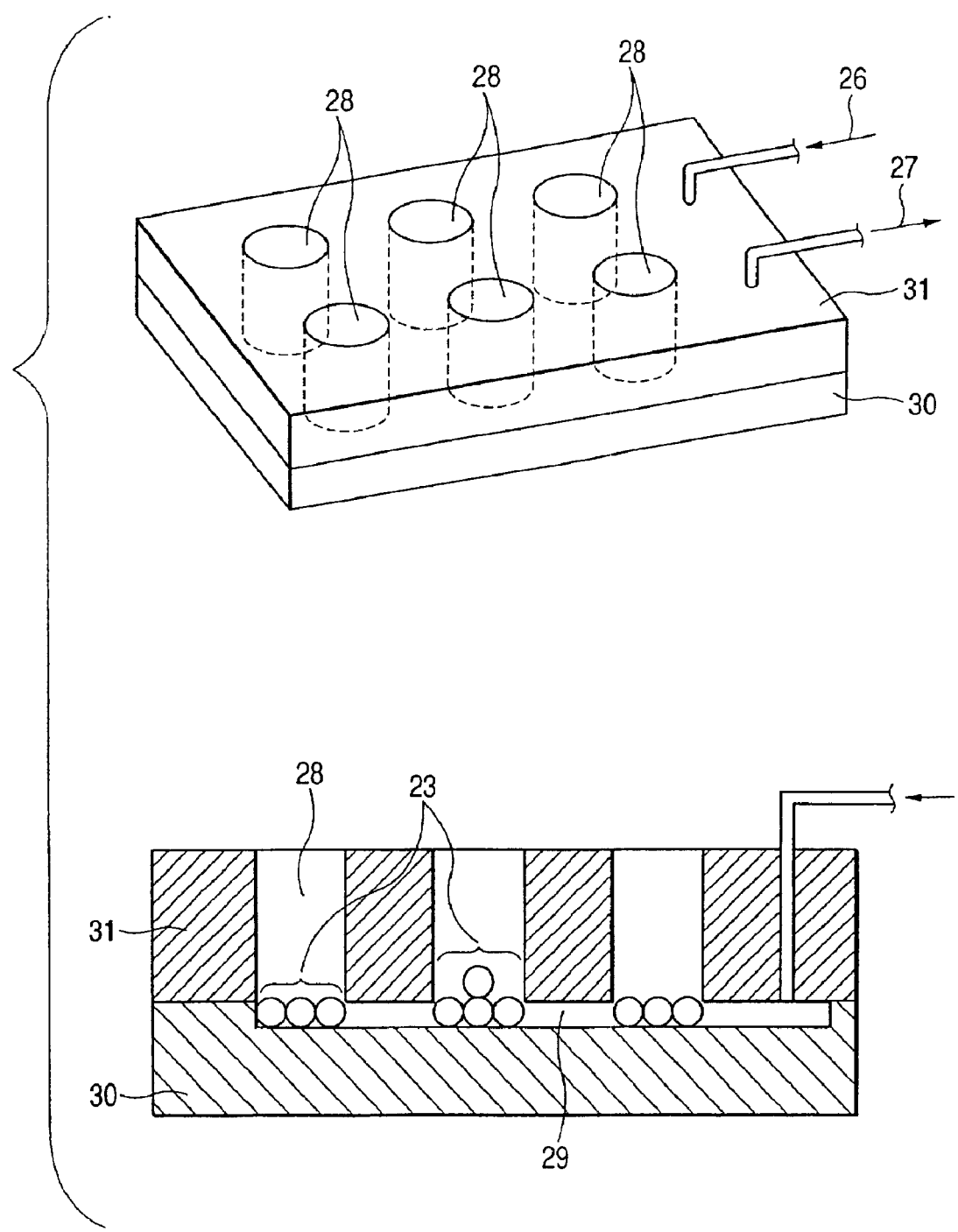
FIG. 10 shows a schematic drawing of another structure example of Example 5 of the present invention showing a conjugate-type reaction chamber module in which beads carrying DNAs and primers are held in a hole made on a board and complementary strand synthesis is carried out.

FIG. 10 is another structure example of Example 5 of the present invention, showing a conjugate-type reaction chamber module used for a DNA sequencing system, in which beads are held in holes formed on a board, a complementary strand is synthesized using DNAs and primers trapped on the beads, and emission produced through reactions with luciferin and so on is detected. The conjugate-type reaction chamber module shown in FIG. 10 is formed by conjugating an upper board 31 comprising a multiple number of holes which form reaction chambers (cells) 28, reagents and washing solution inlet 26 and a solution outlet 27, and a lower board 30 comprising a reaction solution flow route (groove) 29. The upper board 31 and the lower board 30 are conjugated such that the reaction solution flow route 29 is connected to all reaction chambers (cells) 28. As shown in FIG. 10, providing the reaction solution flow route 29 which connects all reaction chambers (cells) 28 is the key point of the simple and convenient reaction device. In the structure shown in FIG. 10, different DNAs are sequenced in different cells but the reaction solution for the sequencing can be supplied and disposed of in combination and simultaneously through the reaction solution flow route 29 formed on the lower board. The depth of the reaction solution flow route 29 is made to be smaller than the diameter of the beads 23. Although the beads 23 carrying DNAs and primers cannot come out from the reaction chamber 28, the reaction solution can be easily injected or removed via the reaction solution flow route 29. In this case, DNAs to be sequenced are immobilized on the beads, but enzymes, such as luciferase, can also be additionally immobilized on the same beads, or alternatively on different beads, or on the wall of the reaction cell. Although not shown in FIG. 10, in the same manner as shown in the structure in FIG. 9, the solution outlet 27 is connected to a waste solution vessel 21 while the reagent and washing solution outlet 26 is connected to reagent reservoirs 1, 2, 3 and 4 which contain a reaction reagent solution and a washing solution reservoir 18, via the introducing-tube conjugate part 19. After introducing reagents from the reagent reservoirs, the inflow is stopped, and then a complementary strand synthesis reaction is carried out. In order to suppress the complementary strand synthesis reaction during the inflow, the reaction vessel is cooled to 20□. Sequencing errors can be also effectively prevented by controlling the temperature to be appropriate during the reaction. Similar to the case with the capillary-type reaction vessel, a reaction solution containing a mixture of dNTP and various reaction reagents is injected in a designated order, a complementary strand is synthesized, pyrophosphate released as a reaction product is converted into ATP, emission occurs with luciferin, and the emission is detected by a light detector. If the lower board 30 is constructed with a transparent material, the emission is detected from the bottom side of the board 30. The chemiluminescence can also detected from the opening side of the cell 28. After the detection, the discharge of the reaction solution and the injection of fresh dNTP are alternately repeated to determine DNA base sequence. In the structure shown in FIG. 10, the liquid flow is made parallel with the bottom line of the lower board 30 of the conjugate type reaction chamber module. However, the reaction solution can flow in and out from the bottom or the upper side of the board. In that case, the bottom is structured with a member with holes through which no beads but liquid can passes.

As described above, according to the present invention, a compact and low-cost DNA sequencing system can be provided by using capillaries or narrow grooves. Further, an extremely large number of DNA samples can be sequenced simultaneously by a simple procedure in which a complementary strand synthesis is carried out using DNAs or primers immobilized on the surface of solids such as beads, the resulting pyrophosphate is converted into ATP, luciferin causes emission, and the location of the emission is monitored. Also, the reaction can be carried out without using dNTP-decomposing enzymes by constructing a reaction chamber as a capillary, a spectral cell or the like through which a reaction solution can be injected or discharged. In that case, errors in sequencing due to an insufficient reaction can be reduced because the complementary strand synthesis reaction can take place thoroughly.

All publication, patents and patent applications cited herein are incorporated herein by reference in their entirety.

What is claimed is:

1. A system for obtaining nucleic acid sequence information comprising:
   a reaction vessel;
   a first capillary or groove supplying dATP into the reaction vessel by pressurizing or by a liquid transfer system
   a second capillary or groove supplying dGTP into the reaction vessel by pressurizing or by a liquid transfer system;
   a third capillary or groove supplying dCTP into the reaction vessel by pressurizing or by a liquid transfer system;
   a forth capillary or groove supplying dTTP into the reaction vessel by pressurizing or by a liquid transfer system; and
   a detector monitoring synthesis of a strand complementary to a template nucleic acid by detecting chemiluminescence which arises from reaction with ATP and luciferin in the presence of luciferase at the reaction vessel the ATP being converted from pyrophosphate produced from the synthesis which uses one of the dATP, the dGTP, the dCTP and the dTTP,
   wherein the template nucleic acid is set in the reaction vessel.

2. The system according to claim 1, wherein the reaction vessel and the first, second, third and fourth capillaries or groves are incorporated into one module.

3. The system according to claim 1, wherein the first, second, third and fourth capillaries or grooves are introduced into a top of the reaction vessel.

4. The system according to claim 1, further comprising dNTP reservoirs each containing one of the dATP, the dGTP, the dCTP and the dTTP and being pressure-controlled to supply one of the dATP, the dGTP, the dCTP and the dTTP contained therein intermittently and repeatedly into the reaction vessel, and an apparatus for controlling electric field between each of the dNTP reservoirs and the reaction vessel.

5. The system according to claim 1, wherein each of the first, second, third and fourth capillaries or grooves has an inner diameter of less than 0.2 mm or a cross-section area less than 0.04 mm$^2$, at an inlet of the reaction vessel.

6. The system according to claim 1, wherein each of the first, second, third and fourth capillaries or grooves has an inner diameter of less than 0.1 mm or a cross-section area less than 0.01 mm$^2$, at an inlet of the reaction vessel.

7. The system according to claim 5, further comprising reagent reservoirs, and reaction solutions each containing one of the dATP, the dGTP, the dCTP and the dTTP being introduced from the reagent reservoirs into the reaction vessel via the first, second, third and fourth capillaries or grooves connected at bottom of the reaction vessel.

8. The system according to claim 5, further comprising a supply unit set on top of the reaction vessel for supplying reaction solutions containing one of the dATP, the dGTP, the dCTP and the dTTP to the reaction vessel and a reaction vessel unit including the reaction vessel, the supply unit and the reaction vessel unit are separable, and the reaction solutions are alternatively and repeatedly supplied from the supply unit via the first, second, third and fourth capillaries or grooves.

9. A nucleic acid analyzing system comprising:

a reaction vessel;

a first capillary or groove supplying dATP into the reaction vessel by pressurizing or by a liquid transfer system;

a second capillary or grove supplying dGTP into the reaction vessel by pressurizing or by a liquid transfer system;

a third capillary or groove supplying dCTP into the reaction vessel by pressurizing or by a liquid transfer system;

a forth capillary or groove supplying dTTP into the reaction vessel by pressurizing or by a liquid transfer system; and a detector monitoring synthesis of a strand complementary to a template nucleic acid by detecting chemiluminescence which arises from reaction with ATP and luciferin in the presence of luciferase at the reaction vessel the ATP being converted from pyrophosphate produced from the synthesis which uses one of the dATP, the dGTP, the dCTP and the dTTP, wherein the template nucleic acid is set in the reaction vessel.

10. The DNA analyzing, system according to claim 9, wherein the detector is capable of distinguishing at least two positions emitting the chemiluminescence.

11. The DNA analyzing system according to claim 9, wherein the detector is an area sensor.

12. The DNA analyzing system according to claim 9, wherein the reaction vessel is selectively shifted relative to the detecting device.

13. The DNA analyzing system according to claim 9, wherein the reaction solutions are supplied substantially simultaneously and independently to the reaction vessel by an ink-jet method.

14. The DNA analyzing system according to claim 12, wherein the detector is a photon multiplier tube or an avalanche photodiode.

* * * * *